United States Patent [19]

Kissiah, Jr.

[11] E Re. 31,031

[45] Reissued Sep. 14, 1982

[54] IMPLANTABLE ELECTRONIC HEARING AID

[76] Inventor: Adam M. Kissiah, Jr., 155 E. Brandy La., Merritt Island, Fla. 32952

[21] Appl. No.: 102,377

[22] Filed: Dec. 11, 1979

Related U.S. Patent Documents

Reissue of:

[64] Patent No.: 4,063,048
Issued: Dec. 13, 1977
Appl. No.: 778,193
Filed: Mar. 16, 1977

[51] Int. Cl.[3] ..... H04R 25/00

[52] U.S. Cl. ..... 179/107 R

[58] Field of Search ..... 128/1 R; 179/107 R, 179/107 BC, 107 E, 107 FD

[56] References Cited

U.S. PATENT DOCUMENTS

| | | | |
|---|---|---|---|
| 3,211,832 | 10/1965 | Putzrath | 179/1 |
| 3,449,768 | 6/1969 | Doyle | 3/1 |
| 3,600,524 | 8/1971 | Biondi et al. | 179/107 R |
| 3,751,605 | 8/1973 | Michelson | 179/107 R |
| 3,752,939 | 8/1973 | Bartz | 179/107 R |
| 4,052,572 | 10/1977 | Schafer | 179/107 R |

OTHER PUBLICATIONS

Archives of Otolaryngology, Jul. 1966, vol. 84, pp. 2-54, "Electrical Stimulation of the Auditory Nerve in Man", F. B. Simmons (reprint).

Proceedings of the First International Conference on Electrical Stimulation of the Acoustic Nerve as a Treatment for Profound Sensorineural Deafness in Man, "Integrated Circuits and Multiple Electrode Arrays", R. L. White, pp. 199-207.

*Laryngoscope*, vol. 86, pp. 1743-1751, "Implantation of Multiple Intracochlear Electrodes for Rehabilitation of Total Deafness: Preliminary Report", C. H. Chouard et al., 1976.

"The Nervous System", D. B. Tower-Editor, vol. 3, Human Communication and its Disorders, 1975, pp. 537-548, Studies on Electrical Stimulation of the Auditory Nerve in Animals and Man, Cochlear Implants, M. M. Merzenich.

Abstracts of the 7th Annual Meeting of the Neuroelectric Society, Nov. 20-23, 1974, New Orleans, Louisiana, pp. 18-19, "Stimuliss-IV-A Multielectrode Implantable Neural Stimulation System", T. Gheewala et al.

IEEE Journal of Solid-State Circuits, vol. SC-10, No. 6, Dec. 1975, "A CMOS Implantable Multielectrode Auditory Stimulator for the Deaf", T. R. Gheewala et al., pp. 472-479.

Proceedings of the Conference on Functional Electrical Stimulation, May 17-19, 1976, pp. 485-498, "Electronics and Electrodes for Sensory Prostheses", R. L. White.

Annals of Otolaryngology, vol. 82, 1973, pp. 473-485, "Electrical Stimulation of the Inner Ear", R. Walloch et al.

Proceedings of the First International Conference on Electrical Stimulation of the Acoustic Nerve as a Treatment for Profound Sensorineural Deafness in Man, 1974, pp. IX, 180, 181; Published by Velo-Bind.

Nordisk Tidsskrift for Medicoteknik, Oct. 1975, English Language Abstract of an Article by Hansen and one page from the article.

*Primary Examiner*—George G. Stellar
*Attorney, Agent, or Firm*—Raymond F. Kramer

[57] ABSTRACT

An electronic hearing aid device for enabling persons having loss of hearing due to a [nonfunctioning] *malfunctioning* inner ear (Cochlea), but [have] *having* a responsive auditory (acoustic, or eighth cranial) nerve, to hear by way of an electronic device including a microphone for receiving audio signals connected to an amplifier for converting the audio signal into an analog voltage signal. The analog voltage signal is filtered by a series of filter networks which separate the analog voltage signal into a plurality of frequency component signals each having a predetermined frequency range within the audio spectrum. The component analog voltage signals are then converted into [digital] pulse signals having the same frequency as the component voltage signal, which are fed to the auditory nerve by way of implanted [platinium] *platinum* (or other) wires, wherein the [digital] pulse signals more accurately simulate the natural sound signals transmitted to the brain for interpretation.

8 Claims, 5 Drawing Figures

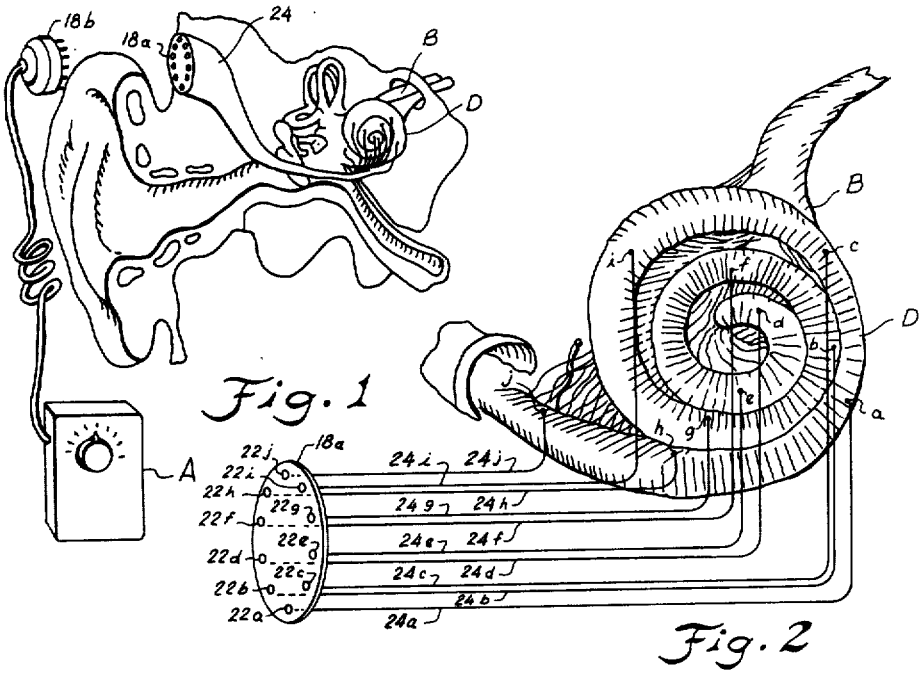
Fig. 1
Fig. 2
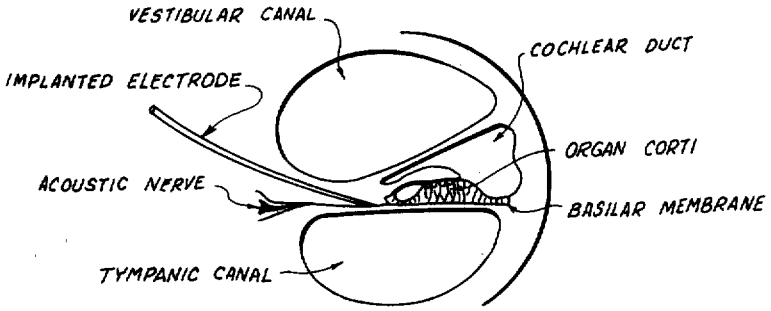
Fig. 2a

IMPLANTABLE ELECTRONIC HEARING AID

Matter enclosed in heavy brackets [ ] appears in the original patent but forms no part of this reissue specification; matter printed in italics indicates the additions made by reissue.

ORIGIN OF THE INVENTION

The invention described herein was made by an employee of the United States Government and may be manufactured and used by or for the Government for governmental purposes without the payment of any royalties thereon or therefor.

*This application is for a reissue of U.S. Pat. No. 4,063,048, issued to Adam M. Kissiah, Jr., the inventor of the subject matter thereof, on Dec. 13, 1977.*

BACKGROUND OF THE INVENTION

This invention relates to an electronic device for improving the hearing of persons who suffer hearing disabilities produced by [non-functioning] *malfunctioning* of the inner ear mechanism. The invention utilizes the principle of implanting [wire] electrodes for transmitting [audio] stimuli signals [directly] to the auditory nerve [.] *system.*

Many of the prior devices developed for hearing aids are cosmetically unattractive and are objectionable in terms of internal noise, buzzing and poor tonal quality. In addition, many prior electronic hearing aids overamplify certain portions of the audio spectrum and underamplify others, resulting in severe distortion of sound.

Furthermore, providing aid for persons who have a [non-functioning] *malfunctioning* inner ear has posed even more difficult problems due to the complex electrical nature of the cochlea[.] *and the associated nerve system.* It has been heretofore proposed that stimulation of the acoustic nerve be accomplished by insertion of hair-size platinum (or other) wires into the cochlea over which an analog voltage is applied representing the audible signal picked up by a miniature microphone. Such a proposal is disclosed in U.S. Pat. No. 3,751,605. However, the analog voltage signal applied to the acoustic nerve [quite often results] *may result* in severe distortion of the original audio signal [and lack of fidelity].

SUMMARY OF THE INVENTION

An electronic hearing aid device for aiding a person having a hearing disability of the inner ear [comprising] *comprises* a receiver for receiving an external audio signal and converting the audio signal into an analog voltage signal. An amplifier is connected to the receiver for receiving the analog voltage signal and amplifying the signal. A plurality of frequency filter networks have inputs connected to the output of the amplifier for receiving the amplified analog voltage signal and breaking the analog signal down into component signals having frequencies corresponding to a predetermined frequency range of each respective filter network. An [analog-digital] *analog-pulse* converter network is connected to the output of each filter network for receiving the component signal therefrom and converting the [component] *analog* signal into a [digital component] *pulsed* signal having a series of digital pulses of the same frequency as the analog component signal[.] *and being of related amplitudes.* A pin connector member is provided having a plurality of pins. Each pin is connected to an output of an [analog-digital] *analog-pulse* filter network for receiving the [digital] pulse signals therefrom. A plurality of electrode members are implanted in the *auditory nerve system, e.g., the* auditory nerve of the inner ear, with an end of *each* one of the electrodes being connected to each of the pins. The distal [end] *ends* of the electrode members are *shown* implanted in the auditory nerve of the inner ear so that each component [digital] *pulse* signal will be applied to stimulate the portion of the nerve normally accustomed to transmitting the same frequency range of audio signals as in the normal hearing process for interpretation in the hearing center of the brain.

Accordingly, an important objective of the present invention is to provide an electronic device for use as an effective hearing aid for people having a hearing disability of the inner ear.

Still another important objective of the present invention is to provide a hearing aid device for persons having a hearing disability in the inner ear which produces [accurate] reproduction of audio signals having [high] *higher perceived* fidelity.

Another important objective of the present invention is to provide an electronic hearing aid device which utilizes discrete electrical stimuli to activate the individual fibers or groups of fibers of the auditory nerve to more naturally [stimulate] *simulate* the true functioning of the inner ear.

Still another important objective of the present invention is to provide an electronic hearing aid device for *overcoming* hearing disabilities of the inner ear, which provides a breakdown of a composite audio signal into a number of component frequency signals within the normal audio spectrum for individually stimulating the auditory nerve fibers, producing a more natural transmission of signals for interpretation [in the normal hearing process] *by the auditory nerve system.*

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 1 is a sectional view illustrating the insertion of a portion of the hearing aid device of the present invention in the human ear, FIG. 2 is an enlarged view of FIG. 1 illustrating the connection of the electrical transmission electrodes of the present invention implanted adjacent the basilar membrane of the inner ear, FIG. 2A is a view of a cross-section of an enlargement of the cochlea (inner ear) showing a *representation of a* proposed access for the distal end of the implanted electrode into the acoustic (eighth [carnial)] *cranial)* nerve.

DESCRIPTION OF A PREFERRED EMBODIMENT

Figure 3:
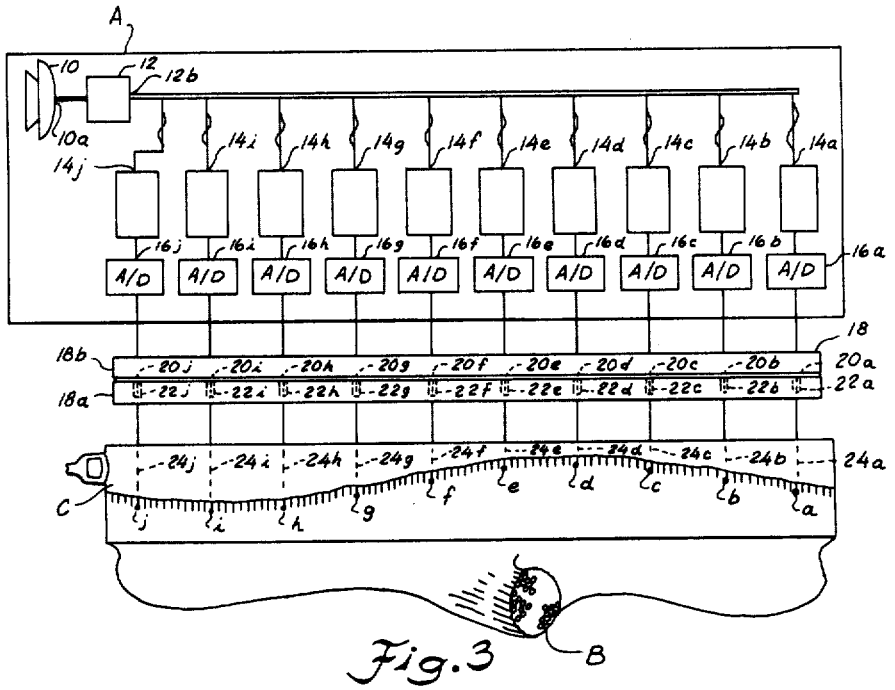
FIG. 3 is a schematic diagram illustrating *a portion of* an electrical circuit for an electronic hearing device constructed in accordance with the present invention.
Figure 4:
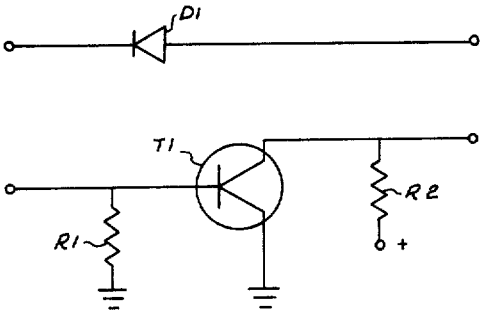
FIG. 4 is a schematic diagram illustrating an analog to [digital] *pulse* converter circuit for use in an electronic hearing aid device constructed in accordance with the present invention.

The invention relates to electronic hearing aid devices for persons who are deaf or suffer partial loss of hearing because of a hearing disability. The present invention is particularly advantageous for aiding persons who have hearing disabilities because of a [non-functioning] *malfunctioning* inner ear, but who still have a responsive auditory nerve system. The proposed device of the present invention will enable these persons to hear by the transmitting of electrical impulses directly to the auditory nerve *system* through [electrode wires] *electrodes* implanted in [the auditory nerve] *such* system. The [non-functioning] *malfunctioning* cochlea [will] *can* be bypassed altogether. The exact method and most appropriate access to the acoustic nerve [must] *should* be experimentally researched and established by the medical profession and those accustomed to the art (otologists). It is essential for optimum performance that electrical insulation be maintained between one implanted electrode and another within the acoustic nerve *system*. In this manner, only those groups of nerves intended for stimulation by a limited band of frequencies will be activated.

[It is considered a major fault of prior attempts at electrode implantation to insert an electrode or electrodes into the cochlear fluid through the oval or round window. The cochlear fluid is not an insulating liquid, and insulation is therefore not maintained between channels.]

In [addition,] prior *hearing aid* devices [have applied] analog voltages *have been applied* to [the] electrodes. The cochlea (inner ear) does not have the capability to convert analog voltages to [digital] pulses for stimulation of acoustic nerve endings. A surgical process for implanting [such] electrodes *in the cochlea* is discussed more fully in an article entitled "The Electric Ear" appearing in the April 1974 issue of Newsweek magazine.

It is to be understood, of course, that other techniques may be utilized for transmitting the electrical impulses generated by the electronic device of the present invention, and that the electronic device of the present invention contemplates application to other types of hearing problems.

Referring now in more detail to the drawings, FIG. 1 illustrates a schematic diagram of an electrical circuit embodying the electronic device of the present invention for receiving external audio sound waves and converting the sound waves into [digital] *pulsed* electrical stimuli which are transmitted [over] *through* the implanted electrodes. A receiver means 10 is provided by a miniature electronic microphone for receiving the external audio signals or sound waves and converting the audio signal into an analog audio voltage signal. The output 10a of the microphone receiver 10 is connected to the input 12a of a conventional amplifier circuit 12 for amplifying the analog voltage signal. A plurality of frequency filter networks 14a through 14j each has an input connected to an output 12b of the amplifier means 12 for receiving the amplified voltage signals therefrom. Each of the frequency filter networks 14a through 14j provides a band-pass filter for passing only a component voltage signal having a frequency of the range to which each respective network is limited.

In the [preferred] *illustrative* embodiment, each frequency filter network provides a band-pass filter in increments or "blocks" of 500 hertz (HZ) over the audio spectrum between 0 and 5,000 hertz. Thus, filter network 14a is designed to pass a signal in the frequency range of from 0 to 500 hertz, filter 14b from 500 to 1,000 hertz, filter 14c from 1,000 to 1,500 hertz, [network] *filter* 14d from 1,500 to 2,000 hertz, filter 14e from 2,000 to 2,500 hertz, filter 14f from 2,500 to 3,000 hertz, filter 14g from 3,000 to 3,500 hertz, filter 14h from 3,500 to 4,000 hertz, filter 14i from 4,000 to 4,500 hertz, and filter 14j from 4,500 to 5,000 hertz. The number of frequency networks used and hence frequency blocks provided for depends on what correlation is to be achieved with natural electrical stimuli of the auditory nerve systems and the number of portions thereof that are to be stimulated.

The composite analog voltage signal coming from amplifier 12 will be passed through the various filter networks 14a through 14j and will be broken down into component signals of 500 hertz "blocks" each, which will be contained within the normal audio spectrum between 0 and 5,000 hertz. The filter networks 14a through 14j may be any conventional band-pass filter such as a crystal or tuned circuit. One suitable type of network circuit is manufactured by the Krohn-Hite Corporation of Avon, Mass., series 3340, specifically model 3343R. This filter represents one of the best in laboratory equipment and exceeds the requirements for the purposes of this invention except in special applications.

Other suitable filter networks may be had within the integrated circuitry art to provide miniature frequency filter networks of the required complexity and capability within the size of a "body" type aid.

One such filter for each of the 10 channels in this instance could be constructed with the use of a resistance-capacitance twin-T [band pass] *band-pass* filter section operating into a high gain tuned audio amplifier, producing a so-called "active filter".

All 10 channels of this type "active filter", along with the microphone and primary audio amplifier, could be packaged within a "body" type hearing aid case, and even within the volume of behind-the-ear and eyeglass [aid] *aids*.

The output of each frequency filter network 14a through 14j is connected to a corresponding [analog-digital] *analog-pulse* converter circuit 16a through 16j. Each of the [analog-digital] *analog-pulse* circuits receives the analog frequency component signal coming from the associated frequency filter network and converts the frequency component signal into a [digital] *pulse* component signal having a series of [digital] pulses of the same frequency as the analog frequency component signal. The [analog-digital] *analog-pulse* converter circuit shown generally at 16a through 16j may be any conventional analog to [digital] *pulse* converter circuit which [will] *may* rectify the analog voltage signal, providing a series of [digital] pulses occurring at the same frequency as the original analog signal.

One suitable converter circuit is comprised of a [simpled] *simple* diode rectifier D1, [or] *and* a transistor gating circuit (or trigger, or switch), whereby a transistor T1 is biased at or slightly below cutoff normally.

When an analog signal from the appropriate filter network (channel) is applied, it will be rectified by the transistor (or diode) switching circuit. Only the positive going portion of the audio sine wave will cause the transistor to conduct. The turn-on threshold of the transistor can therefore be adjusted to allow control of input analog voltage levels, and thus control of background noise.

Voltage level control and time duration limits may also be included in the transistor output [(Collector)] *(collector)* circuitry, thus maintaining [strict] control of voltage levels and pulse widths applied to the acoustic nerve *system*.

Each of the [analog-digital] *analog-pulse* converter circuits 16a through 16j is connected to a pin connector member 18 having a plurality of pin connections 20a through 20j connected to the corresponding [analog-digital] *analog-pulse* converter circuits 16a through 16j for receiving the [digital] *pulsed* component signal therefrom. The pin connector member 18 is preferably in the form of a female connector 18a which may be implanted in the area of the mastoid bone of the outer ear such as shown in FIG. 1, and a male connector member 18b wherein the pins 20a through 20j are carried by the male connector for insertion into a plurality of matching insert channels 22a through 22j carried within the female connector 18a. In this manner, the electronic circuit elements of the present invention may be removably attached and replaced as a hearing aid device.

It should be noted that another method of female connector implantation [could] *might* be accomplished by placing it in the ear canal. Implantation in the ear canal may be more cosmetically acceptable than location in the mastoid area.

Connected to the insert channels 22a through 22j of the female coupling 18a are a plurality of corresponding electrode members 24a through 24j which have their remote [end] *ends* surgically implanted adjacent portions of the auditory nerve system B of the inner ear along the basilar membrane C at points a through j. The electrodes transmit each component [digital pulse] *pulsed* signal at the same portion of the auditory nerve normally accustomed to transmitting like signals in the normal hearing process for interpretation in the hearing center of the brain. Thus, each individual block of [digital] impulse stimuli will be applied directly to the auditory nerve *system* by way of the imbedded electrodes 24a through 24j which are preferably in the form of platinum wires.

[The] *It is proposed that the pulsed stimuli of the* electronic device constructed in accordance with the present invention [proposes that the digital stimuli] will more naturally and accurately simulate the functioning of the electrical nature of the cochlea D output to the auditory nerve system. Of course, the microphone 10, the amplifier 12, the frequency filter networks 14a through 14j, and the [analog-to-digital] *analog-to-pulse* converter circuits 16a through 16j, and a suitable power source will be appropriately packaged external to the patient in a package housing A.

It is important to note that the greater the number of individual channels (wires), and thus the greater the synthesis of the input audio signal, then the better the fidelity, or true reproduction of the input signal (s), or tone (s).

The ten individual channels presented in this invention may exceed the current practical state-of-the-art in electrode implantation within the acoustic nerve. The number ten is therefore illustrative, and not intended to be a limitation to the concept.

Likewise, neither is utilization of the audio spectrum between 0–5,000 hertz.

The most beneficial frequency range required by various patients will vary in each case and [must] *should* be determined by an audiologist.

Thus, it can be seen that an advantageous construction for a hearing aid device can be had in accordance with the present invention for aiding a person having a hearing disability of the inner ear. By breaking down a composite audio signal into component "blocks" of a predetermined frequency range and [digitizing] *converting* each block component of the audio signal *into a series of pulses* for direct application to the auditory nerve *system* by way of imbedded [platinum wires] *electrodes*, a more natural and accurate simulation of the true functioning of the inner ear can be accomplished.

While a preferred embodiment of the invention has been described, using specific terms, such description is for illustrative purposes only, and it is to be understood that changes and variations may be made without departing from the spirit or scope of the following claims.

What is claimed is:

1. An electronic hearing aid device for use in aiding a person having a [non-functioning] *malfunctioning* inner ear mechanism comprising:

receiver means for receiving an external audio signal and converting said signal into an analog voltage signal;

amplifier means connected to said receiver means for receiving said analog voltage signal and amplifying said voltage signal;

a plurality of frequency filter networks each having an input connected to an output of said amplifier means for receiving said amplified voltage signal and filtering said analog signal into a number of separate frequency component signals corresponding to a predetermined frequency range of each respective filter network;

[analog-digital] *analog-pulse* converter circuit means connected to the output of each filter network for receiving each said frequency component signal and converting said signal into a [digital] *pulsed* component signal; and a plurality of [elongated] electrode members each having one end connected to an output of one of said converter circuit means with the remote end thereof adapted for being implanted adjacent a portion of the auditory nerve system [of the inner ear] for transmitting said [digital] *pulsed* component signals for interpretation in the hearing portion of the brain.

2. The device as set forth in claim 1 wherein said [analog-digital convertor] *analog-pulse converter* circuit means converts said frequency component signal into a series of [digital] pulses occurring at the same frequency as said frequency component signal.

3. The device as set forth in claim 1 wherein said electrodes are platinum wires.

4. The device as set forth in claim 1 further comprising pin collector means having a plurality of pins for connection of said output of said converter circuit means and said one end of said electrodes.

5. The device as set forth in claim 4 wherein said connector means includes a female connector for being implanted adjacent the mastoid bone portion of the outer ear having a plurality of pin channels connected to said electrodes and a male connector having corresponding pin connections connected to said converter circuit outputs for insertion into said pin channels of said female connector.

6. An electronic hearing aid device for aiding a person having a [non-functioning] *malfunctioning* inner ear comprising:

receiver means for receiving an audio signal and converting said signal into an analog voltage signal;

amplifier means connected to the receiver means for receiving said analog voltage signal and amplifying said signal;

a plurality of frequency filter networks having an input connected to the output of said amplifier means for receiving said amplified analog voltage signal and separating said analog signal into frequency component signals having frequencies corresponding to a predetermined frequency range of each respective filter network;

an [analog-digital] *analog-pulse* converter network connected to the output of each of said filter networks for receiving said analog frequency component signal therefrom and converting said frequency component signal into a [digital] *pulsed* component signal having a series of [digital] pulses of the same frequency as the analog frequency component [signal] *and being of related amplitudes*;

a pin connector member having a pin connection connected to an output of each [analog-digital] *analog-pulse* filter network for receiving said [digital] pulse signals; and a plurality of electrode members for being implanted adjacent portions of the nerve of the inner ear with the remote end of said electrodes being connected to each of said pin connections so that each component [digital] pulse signal will be applied at the same portion of the nerve normally accustomed to transmitting like signals in the normal hearing process for interpretation as sound.

*7. An electronic hearing aid for use in aiding a person having a malfunctioning hearing mechanism to hear comprising:*

*receiver or microphone means for receiving an external audio signal and converting said signal into an analog voltage signal;*

*amplifier means connected to said receiver means for receiving said analog voltage signal and amplifying it;*

*a plurality of filters, each having inputs thereof connected to the output of said amplifier means, for receiving said amplified voltage signal and filtering said signal into a plurality of separate component signals corresponding to separate frequency ranges;*

*analog-pulse converter circuit means connected to the output of each filter network for receiving each said frequency component signal and converting said signal into a pulsed component signal; and*

*a plurality of electrodes, each being connected to an output of said converter circuit means and having at least a portion thereof adapted for implantation adjacent a portion of the auditory nerve system, so that the electrodes transmit pulsed frequency component signals to the auditory nerve system for interpretation in the hearing portion of the brain.*

*8. A device according to claim 7 wherein the analog-pulse converter circuit is one which produces a unipolar pulsed component signal.*

* * * * *